United States Patent
Mostapha et al.

(10) Patent No.: US 12,175,636 B2
(45) Date of Patent: Dec. 24, 2024

(54) RECONSTRUCTION WITH USER-DEFINED CHARACTERISTIC STRENGTH

(71) Applicant: Siemens Healthineers AG, Forchheim (DE)

(72) Inventors: Mahmoud Mostapha, Princeton, NJ (US); Boris Mailhe, Plainsboro, NJ (US); Marcel Dominik Nickel, Herzogenaurach (DE); Gregor Körzdörfer, Erlangen (DE); Simon Arberet, Princeton, NJ (US); Mariappan S. Nadar, Plainsboro, NJ (US)

(73) Assignee: Siemens Healthineers AG, Forchheim (DE)

( * ) Notice: Subject to any disclaimer, the term of this patent is extended or adjusted under 35 U.S.C. 154(b) by 632 days.

(21) Appl. No.: 17/484,017

(22) Filed: Sep. 24, 2021

(65) Prior Publication Data

US 2023/0095222 A1    Mar. 30, 2023

(51) Int. Cl.
*G06T 5/70* (2024.01)
*G06N 3/04* (2023.01)
*G06T 11/00* (2006.01)
*G16H 30/40* (2018.01)

(52) U.S. Cl.
CPC .............. *G06T 5/70* (2024.01); *G06N 3/04* (2013.01); *G06T 11/005* (2013.01); *G16H 30/40* (2018.01); *G06T 2207/10088* (2013.01)

(58) Field of Classification Search
CPC .............. G06T 5/70; G06T 11/005; G06T 2207/10088; G06N 3/04; G16H 30/40
See application file for complete search history.

(56) References Cited

U.S. PATENT DOCUMENTS

| | | | |
|---|---|---|---|
| 2007/0053477 A1* | 3/2007 | Ning | G06T 5/70 378/4 |
| 2015/0371372 A1* | 12/2015 | Athavale | A61B 5/055 382/131 |
| 2016/0292878 A1* | 10/2016 | Hsieh | G06T 11/008 |
| 2018/0005415 A1* | 1/2018 | Wang | G06T 11/005 |
| 2019/0057523 A1* | 2/2019 | Cao | G06T 11/006 |
| 2019/0172230 A1 | 6/2019 | Mailhe et al. | |
| 2019/0236763 A1* | 8/2019 | Chan | A61B 6/032 |
| 2020/0311878 A1* | 10/2020 | Matsuura | G06F 18/2115 |
| 2020/0408864 A1* | 12/2020 | Mailhe | G06N 3/088 |
| 2021/0076972 A1* | 3/2021 | Novikov | G01R 33/5608 |

(Continued)

OTHER PUBLICATIONS

Wu, Defau et al, Consensus Neural Network for Medical Imaging Denoising with Only Noisy Training Samples, Jun. 9, 2019, Arxiv.org, pp. 1-9 (Year: 2019).*

(Continued)

*Primary Examiner* — Lewis G West

(57) ABSTRACT

For reconstruction in medical imaging, user control of a characteristic (e.g., noise level) of the reconstructed image is provided. A machine-learned model alters the reconstructed image to enhance or reduce the characteristic. The user selected level of characteristic is then provided by combining the reconstructed image with the altered image based on the input level of the characteristic. Personalized or more controllable impression for medical imaging reconstruction is provided without requiring different reconstructions.

12 Claims, 4 Drawing Sheets

(56) References Cited

U.S. PATENT DOCUMENTS

2021/0150783 A1    5/2021  Arberet et al.
2022/0107379 A1*   4/2022  Takeshima ......... G01R 33/3621
2022/0375038 A1*  11/2022  Nagare ................. G06V 10/30

OTHER PUBLICATIONS

U.S. Appl. No. 17/155,630, filed Jan. 22, 2021.
U.S. Appl. No. 17/303,790, filed Jun. 8, 2021.
U.S. Appl. No. 17/473,229, filed Sep. 13, 2021.

* cited by examiner

RECONSTRUCTION WITH USER-DEFINED CHARACTERISTIC STRENGTH

FIELD

This disclosure relates to medical image reconstruction, such as reconstruction in magnetic resonance (MR) imaging.

BACKGROUND

Some types of medical imaging perform reconstruction for imaging, such as MR, computed tomography (CT), positron emission tomography (PET), or single photon emission computed tomography (SPECT). Reconstruction may output information with a different impression or look-and-feel than desired by some users. Where sparse sampling is used, the reconstruction to provide user-desirable imaging may be difficult. For example, parallel Imaging (PI) combined with compressed sensing (CS) techniques can allow much faster MR imaging scan times but results in images that may not be desirable to all users.

Despite recent success of machine-learned accelerated MR reconstruction models, there is no consensus on an optimal image impression such as noise level, perceived sharpness, etc. The desired image (e.g., level of noise verses sharpness) typically varies depending on the radiologist preference and the targeted application.

One way to solve this problem is by training separate reconstruction models for pre-defined discrete denoising levels, which is typically accomplished by adding different noise levels (mainly Gaussian noise) to the training data to perform the required denoising level. However, such an approach only allows for a discrete set of denoising levels with the burden of multiple trained models to maintain. Moreover, the approach also lacks the flexibility to deal with spatially variant noise, limiting their applications in practical denoising.

SUMMARY

By way of introduction, the preferred embodiments described below include methods, systems, instructions, and computer readable media for reconstruction in medical imaging. User control of a characteristic (e.g., noise level) of the reconstructed image is provided. A machine-learned model alters the reconstructed image to enhance or reduce the characteristic. The user selected level of characteristic is then provided by combining the reconstructed image with the altered image based on the input level of the characteristic. Personalized or more controllable impression for medical imaging reconstruction is provided without requiring different reconstructions.

In a first aspect, a method of reconstruction for a medical imaging system is provided. A patient is scanned by the medical imaging system. The scanning acquires scan data. An object of the patient is reconstructed from the scan data. The object is represented by first reconstruction data from the reconstructing. The reconstruction data is denoised. The reconstruction data is denoised by application to a machine-learned denoising network. The object is represented by second reconstruction data from the denoising. A user-selected level of denoising is received. The first and second reconstruction data are combined based on the user-selected level of denoising. An image of the object from the combination of the first and second reconstruction data is displayed.

In one embodiment, the scanning is magnetic resonance scanning pursuant to a protocol for parallel imaging with compressed sensing. In some embodiments, the reconstructing is with a machine-learned model, such as an unrolled iterative reconstruction where the machine-learned model implements a regularization function of the unrolled iterative reconstruction. In another embodiment, the machine-learned denoising network was trained independently of the machine-learned model where the machine-learned denoising network used outputs of the machine-learned model with the weights of the machine-learned model fixed in the training of the machine-learned denoising network.

In one approach, the denoising includes inputting the first reconstruction data into the machine-learned denoising network. The machine-learned denoising network outputs the second reconstruction data in response to the inputting.

Various machine-learned denoising networks or models may be used. For example, the machine-learned denoising network is an image-to-image network, such as a deep iterative hierarchal network.

Any range over continuous or discontinuous values may be used for the user-selected level of denoising. For example, the user-selected level of denoising is a value of a continuous variable in a range of [0,1].

Where the user seeks a different impression, the user may tune the level of denoising. For example, the user-selected level of denoising is received as an adjustment to tune the image based on a previous value of the user-selected level of denoising.

Various combinations of the first and second reconstruction data may be used. In one embodiment, the combination is a linear interpolation between the first and second reconstruction data.

In one embodiment, the image is displayed where the image has a level of noise relative to sharpness based on the user-selected level of denoising.

In a second aspect, a system is provided for reconstruction in medical imaging. A medical scanner is configured to scan a region of a patient. The scan provides scan data. An input is provided to receive a level of a characteristic. An image processor is configured to reconstruct a first representation of the region, to alter the characteristic of the first representation by application to a machine-learned model, the alteration resulting in a second representation of the region, to combine first and second representations based on the level of the characteristic, the combination resulting in a third representation. A display is configured to display an image of the region from the third representation.

In one embodiment, the medical scanner is a magnetic resonance scanner having multiple receive coils. The scan data is scan data from a parallel imaging with the multiple receive coils using compressed sensing.

In other embodiments, the image processor is configured to reconstruct with a deep-learnt model. The machine-learned model for altering the characteristic may be any of various models, such as a convolutional neural network (e.g., a deep iterative hierarchal network.)

Various characteristics may be controlled. For example, the characteristic is the relative noise and sharpness. The machine-learned model is a denoising model. The image processor is configured to combine as a linear function weighted by the level of the relative noise and sharpness.

In a third aspect, a method of reconstruction is provided for a medical imaging system. A patient is scanned by the medical imaging system. The scanning acquires scan data. An object of the patient is reconstructed from the scan data. A characteristic of the reconstructed object is altered by application of the reconstructed object to a machine-learned network. The reconstructed object is combined with an output of the machine-learned network based on an input level. An image from the combination is displayed.

In one embodiment, the reconstruction is with a machine-learned model. The alteration includes denoising where the machine-learned network is a deep iterative hierarchal network for the denoising. The combination is with a linear interpolation weighted by the input level.

The present invention is defined by the following claims, and nothing in this section should be taken as a limitation on those claims. Further aspects and advantages of the invention are discussed below in conjunction with the preferred embodiments and may be later claimed independently or in combination.

DETAILED DESCRIPTION

Reconstruction, such as MR reconstruction, is provided with a user-defined strength of a characteristic. The strength, such as for denoising, may be a continuous variable. Output is generated with varying levels (e.g., denoising). The desired level is provided according to a user-defined parameter by interpolating between outputs (e.g., an intermediate) at different stages of a single reconstruction.

Use of multiple reconstructions from the same scan data is avoided. Mixing the results of separate reconstructions for generating images at intermediate levels would result in longer reconstruction times since at least two reconstruction algorithms would have to be executed. Additionally, on a pixel level, correspondence between two images cannot be guaranteed, which runs the risk of generating interpolated images with unnatural or hallucinated intensities. Having a bank of selectable reconstruction algorithms requires multiple reconstruction passes to change or tune the level.

The proposed solution adds a user-defined strength input or level, which controls the output. Such a parameter allows for convex combinations of, for example, a sharp but noisy output produced by a deep-learned reconstruction network and a corresponding smoothed version made by passing the noisy output through a deep-learned image denoiser followed by a data-consistency layer. An efficient reconstruction algorithm design is utilized while enabling handling of multiple user-defined parameters, such as image denoising strength. A wide range of data variability may be processed with a single model. The continuous, user-defined denoising strength enjoys several desirable properties, including: the ability to handle a wide range of noise levels effectively with a single network, the ability to remove spatially variant noise by learning noise maps from heterogeneous MRI datasets, flexibility to adapt to data with different signal-to-noise (SNR) levels (e.g., from low-cost scanners) by re-tuning the desired denoising level or re-training the image denoiser with few shots, and/or flexibility to adjust denoising strength to user preference and to the acquisition protocol for a given application. The resulting image perception may be adjusted individually, allowing the same reconstruction approach to provide desired impression for a variety of users or viewers.

Figure 1:
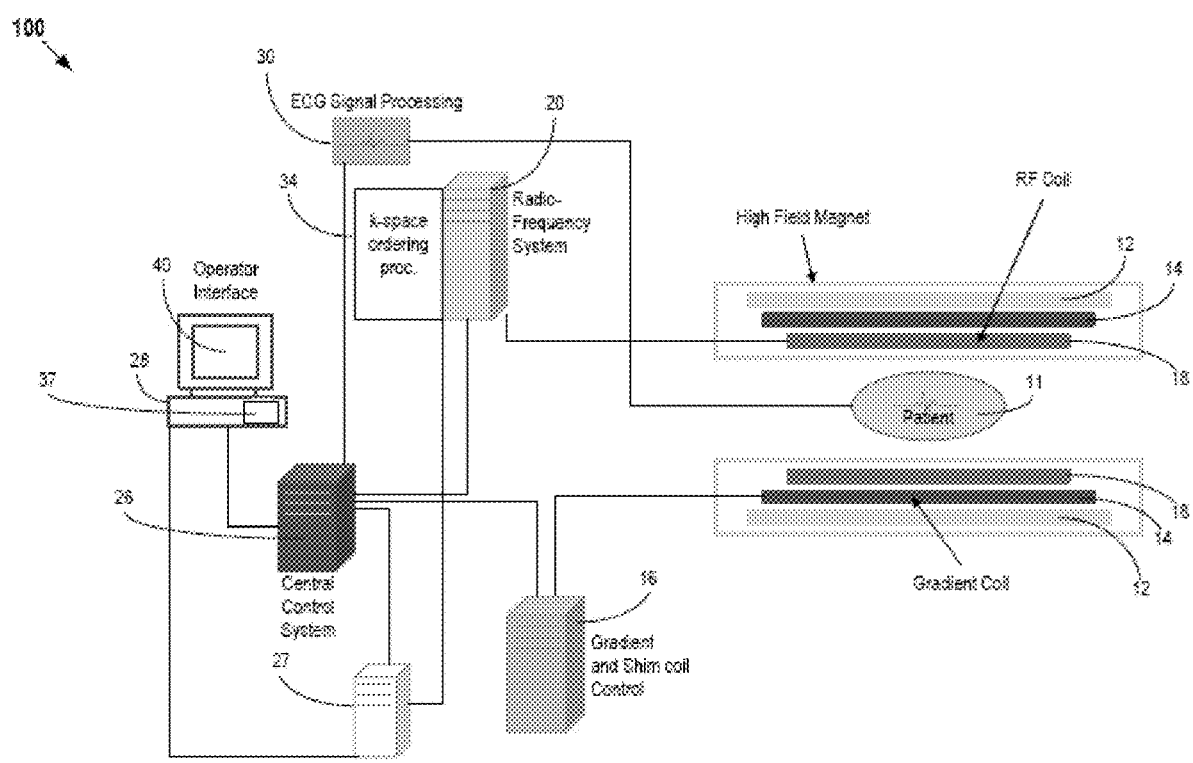
FIG. 1 is a block diagram of an embodiment of an MR system for medical imaging with reconstruction having input control of a characteristic of the image.

FIG. 1 shows one embodiment of a system for reconstruction in medical imaging. The system scans a given patient, and then reconstructs a representation of the patient from the scan. A machine-learned model is applied to alter the representation, providing two representations of available extremes with respect to a characteristic, such as noise level. The representations may be combined based on a user or input weight, allowing creation or tuning of an intermediate between the extremes. The impression (e.g., noise level) is controllable based on a single application of reconstruction.

The system is described below in general, with a following method providing other details. The system implements the method of FIG. 2, the model of FIG. 3, or another method.

The example used herein is in a MR context (i.e., a MR scanner), but other types of scanner may be used (e.g., reconstruction for CT, PET, SPECT, or other medical imaging).

The system is implemented by an MR scanner or system, a computer based on data obtained by MR scanning, a server, or another processor. MR scanning system 100 is only exemplary, and a variety of MR scanning systems can be used to collect the MR data. The MR scanner 100 is configured to scan a patient. The scan provides scan data in a scan domain. The system 100 scans a patient to provide k-space measurements (measurements in the frequency domain).

In the system 100, magnetic coils 12 create a static base magnetic field in the body of patient 11 to be positioned on a table and imaged. Within the magnet system are gradient coils 14 for producing position dependent magnetic field gradients superimposed on the static magnetic field. Gradient coils 14, in response to gradient signals supplied thereto by a gradient and shim coil control module 16, produce position dependent and shimmed magnetic field gradients in three orthogonal directions and generate magnetic field pulse sequences.

RF (radio frequency) module 20 provides RF pulse signals to RF coil 18, which in response produces magnetic field pulses that rotate the spins of the protons in the imaged body of the patient 11 by ninety degrees, by one hundred and eighty degrees for so-called "spin echo" imaging, or by angles less than or equal to 90 degrees for so-called "gradient echo" imaging. Gradient and shim coil control module 16 in conjunction with RF module 20, as directed by central control unit 26, control slice-selection, phase-encoding, readout gradient magnetic fields, radio frequency transmission, and magnetic resonance signal detection, to acquire magnetic resonance signals representing planar slices of patient 11.

In response to applied RF pulse signals, the RF coil 18 receives MR signals, i.e., signals from the excited protons within the body as they return to an equilibrium position established by the static and gradient magnetic fields. The RF coil 18 may be a whole-body coil or may be formed from one or more local coils, at least on receive. The MR signals are detected and processed by a detector within RF module 20 and k-space component processor unit 34 to provide an MR dataset to an image data processor for processing into an image (i.e., for reconstruction in the object domain from the k-space data in the scan domain). In some embodiments, the image processor is in or is the central control unit 26. In other embodiments, such as the one depicted in FIG. 1, the image processor is in a separate unit 27. ECG synchronization signal generator 30 provides ECG signals used for pulse sequence and imaging synchronization. A two- or three-dimensional k-space storage array of individual data elements in k-space component processor unit 34 stores corresponding individual frequency components forming an MR dataset. The k-space array of individual data elements has a designated center, and individual data elements individually have a radius to the designated center.

A magnetic field generator (comprising coils 12, 14 and 18) generates a magnetic field for use in acquiring multiple individual frequency components corresponding to individual data elements in the storage array. A storage processor in the k-space component processor unit 34 stores individual frequency components acquired using the magnetic field in corresponding individual data elements in the array. The row and/or column of corresponding individual data elements alternately increases and decreases as multiple sequential individual frequency components are acquired. The magnetic field acquires individual frequency components in an order corresponding to a sequence of substantially adjacent individual data elements in the array, and magnetic field gradient change between successively acquired frequency components is substantially minimized.

The central control unit 26 uses information stored in an internal database to process the detected MR signals in a coordinated manner to generate high quality images of a selected slice(s) of the body (e.g., using the image data processor) and adjusts other parameters of the system 100. The stored information includes a predetermined pulse sequence of an imaging protocol and a magnetic field gradient and strength data as well as data indicating timing, orientation, and spatial volume of gradient magnetic fields to be applied in imaging.

The medical scanner 100 is configured by the imaging protocol to scan a region of a patient 11. For example, in MR, such protocols for scanning a patient for a given examination or appointment include diffusion-weighted imaging (acquisition of multiple b-values, averages, and/or diffusion directions), turbo-spin-echo imaging (acquisition of multiple averages), or contrast. In one embodiment, the protocol is for compressed sensing. The k-space is under sampled for more rapid scanning of the patient. The reconstruction may still reconstruct a representation in the object domain from the under sampled k-space data, but the representation may be more likely to suffer from noise. In another embodiment, parallel imaging is used. Multiple local coils are used to receive the data, providing additional information for reconstruction. In yet another embodiment, the protocol is for parallel imaging with compressed sensing.

The system 100 includes an operator interface 40, formed by an input and an output. The input may be an interface, such as interfacing with a computer network, memory, database, medical image storage, or other source of input data. The input may be a user input device, such as a mouse, trackpad, keyboard, roller ball, touch pad, touch screen, or another apparatus for receiving user input. The input receives the level of characteristic, such as a denoising level. An individual may input the level, such as manually or physically entering the level. Previously used levels may be input from the interface. Default, institution, facility, or group set levels may be input, such as from memory to the interface.

The output is a display device but may be an interface. The final and/or intermediate images reconstructed from the scan are displayed. For example, an image of a region of the patient tuned based on the input level of denoising is displayed. A generated image of the reconstructed representation (e.g., combined representation) for a given patient is presented on a display of the operator interface 40. The image is from a combination of the representations from reconstruction and from the alteration of the reconstruction.

The display is a CRT, LCD, plasma, projector, printer, or other display device. The display is configured by loading an image to a display plane or buffer. The display is configured to display the reconstructed MR image of the region of the patient. The computer 28 of the operator interface forms a graphical user interface (GUI) enabling user interaction with the central control unit 26 and enables user modification in substantially real time. The display processor 37 processes the magnetic resonance signals to provide image representative data for display on display device, for example.

The central control unit 26 (i.e., controller) and/or processor 27 is an image processor that reconstructs a representation of the patient from the k-space data. The image processor is a general processor, digital signal processor, three-dimensional data processor, graphics processing unit, application specific integrated circuit, field programmable gate array, artificial intelligence processor, digital circuit, analog circuit, combinations thereof, or another now known or later developed device for reconstruction. The image processor is a single device, a plurality of devices, or a network. For more than one device, parallel or sequential division of processing may be used. Different devices making up the image processor may perform different functions, such as reconstructing by one device and volume rendering by another device. In one embodiment, the image processor is a control processor or other processor of the MR scanner 100. Other image processors of the MR scanner 100 or external to the MR scanner 100 may be used.

The image processor is configured by software, firmware, and/or hardware to reconstruct. The image processor operates pursuant to instructions stored on a non-transitory medium to perform various acts described herein.

The image processor is configured to reconstruct a representation of a scan region, such as a region of the patient. The image processor is configured to reconstruct a representation in an object domain. The representation or object in the object domain is reconstructed from the scan data in the scan domain. The scan data is a set or frame of k-space data from a scan of the patient. The object domain is an image space and corresponds to the spatial distribution of the patient. A planar or volume representation or object is reconstructed as an image representing the patient. For example, pixels values representing tissue in an area or voxel values representing tissue distributed in a volume are generated.

The system 100 performs reconstruction. The reconstruction may be a traditional approach or optimization (e.g., not machine-learning based), such as generalized autocalibrating partially parallel acquisitions (GAPPA). In other embodiments, the reconstruction is performed, at least in part, using a machine-learned model. The machine-learned model is formed from one or more networks and/or another machine-learned arrangement (e.g., support vector machine). For an example used herein, the machine-learned model is a deep-learned neural network. The machine-learned model is used for at least part of the reconstruction, such as regularization of reconstruction. In regularization, image or object domain data is input, and image or object domain data with less artifact is output. The remaining portions or stages of the reconstruction (e.g., Fourier transform and gradients in iterative optimization) are performed using reconstruction algorithms and/or other machine-learned networks. In other embodiments, the machine-learned model is used for all the reconstruction operations (one model to input k-space data and output regularized image data) or other reconstruction operations (e.g., used for transform, gradient operation, and/or regularization). The reconstruction is of an object or image domain from projections or measurements in another domain, and the machine-learned model is used for at least part of the reconstruction.

In some embodiments, an unrolled iterative reconstruction is provided as alternating gradient updates and regularization where a machine-learned network is provided for regularization through iteration sequences. A given iteration either in an unrolled network or through a repetition of the reconstruction operations includes a gradient update and regularization. The gradient update compares the current image object with the scan data (e.g., k-space measurements). This comparison uses a system transform to relate the measurements to the image object. Any gradient or comparison relating the image object to the measurements may be used. Regularization is provided in one, some, or all the iterations and can include the application of a network.

Filtering and/or other operations for reconstruction and/or post-reconstruction may be provided. Input bias field correction and/or extrapolation for momentum may be provided as part of the reconstruction. In other embodiments, the reconstruction is performed without iteration.

The image processor is configured to alter a characteristic of the reconstructed representation. For example, a reconstruction may have an undesired level of noise in an effort to have more sharpness (i.e., relative noise and sharpness). As other examples, the visibility of particular types of anatomy, lesions, or regions may vary. In other examples, noise is provided regardless of a level of sharpness. The reconstruction or representation is altered to adjust this characteristic. The alteration results in another representation having more or less of the characteristic, such as less noise.

The alteration is provided by application to a machine-learned model. For example, the machine-learned model is a denoising model. The image processor is configured to reduce a level of noise in the reconstructed representation.

Various machine-learned models may be used, such as a neural network or support vector machine. In one embodiment, the machine-learned model for altering the characteristic is a convolutional neural network, such as an image-to-image network or U-Net. A deep iterative hierarchal network (DIHN) may be used.

The image processor is configured to combine the representations. The representation output by the reconstruction and the altered representation are combined. The combination may be selection of one of the two representations as extremes or may be by interpolation, averaging, summation, or other combination to form an intermediate representation. In one embodiment, a linear function or interpolation is used for the combination.

The input level of the characteristic (e.g., a weight in the range 0,1) is used for the combination. The amount of influence of one representation relative to the other is set based on the input (e.g., weighting by the level of relative noise and sharpness). The combination is performed for each pixel or voxel from the two representations. The same weight or level is used for each pixel or voxel. In other embodiments, a weight map is used. The level of characteristic received at the input defines the level spatially where different locations have different weights (i.e., one-, two-, or three-dimensional variation in the weight is input). The combination results in a third representation tuned to the input level.

The resulting representation may be a complex or real image. The output combined representation is the final combined representation. The output image represents the patient (i.e., a reconstructed representation). The image processor may be configured to generate an MR image from the combined representation. Where the representation is of an area, the values of the representation may be mapped to display values (e.g., scalar values to display color values) and/or formatted for display (e.g., interpolated to a display pixel grid). Alternatively, the output representation is of display values in the display format. Where the representation is of a volume, the image processor performs volume or surface rendering to render a two-dimensional image from the voxels of the volume. This two-dimensional image may be mapped and/or formatted for display as an MR image. Any MR image generation may be used so that the image represents the measured MR response from the patient. The image represents a region of the patient.

Figure 2:
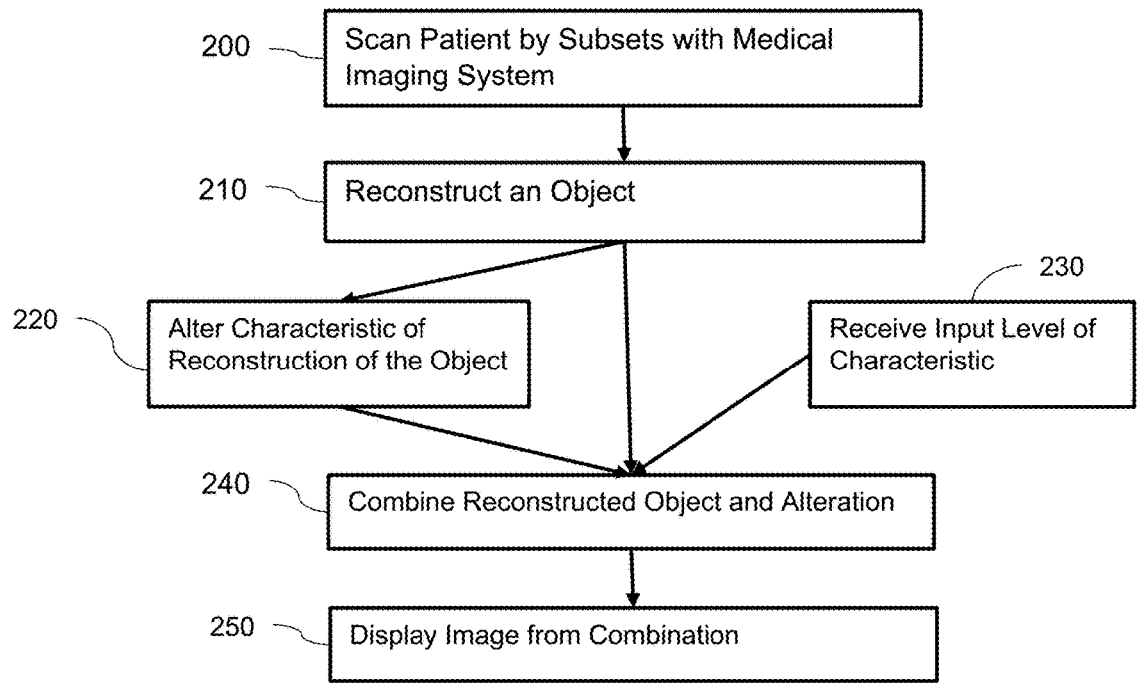
FIG. 2 is a flow chart diagram of one embodiment of a method for reconstruction with a machine-learned model used for control of a characteristic of the output image.

FIG. 2 is a flow chart diagram of one embodiment of a method for reconstruction of a medical image in a medical imaging system, such as reconstruction of a MR image in an MR system. A machine-learned model as trained is applied to the representation output from reconstruction, forming another version of the reconstruction with one or more characteristics altered. The output reconstruction and altered reconstruction have different levels of the one or more characteristics and may then be combined to form a final reconstruction with a selectable level or levels of the one or more characteristics.

During application to one or more different patients and corresponding different scan data, the same learned weights or values of the machine-learned model for altering the characteristic are used. The model and values for the learnable parameters are not changed from one patient to the next, at least over a given time (e.g., weeks, months, or years) or given number of uses (e.g., tens or hundreds). These fixed values and corresponding fixed model are applied sequentially and/or by different processors to scan data for different patients. The model may be updated, such as retrained, or replaced but does not learn new values as part of application for a given patient.

The method is performed by the system of FIG. 1 or another system. The medical scanner scans the patient. A user input or other input receives an input level of a characteristic. An image processor reconstructs an object, alters a characteristic of the reconstruction, and combines reconstructions based on the received input level. A display displays the medical image resulting from the combination of reconstructions. Other components may be used, such as a remote server or a workstation performing the reconstruction, combination, and/or display.

The method is performed in the order shown or other orders. Additional, different, or fewer acts may be provided. For example, a preset, default, or user input settings are used to configure the scanning prior art act 200. As another example, the image is stored in a memory (e.g., computerized patient medical record) or transmitted over a computer network instead of or in addition to the display of act 250.

In act 200, the medical imaging system scans a patient. The scan is guided by a protocol, such as parallel imaging with compressed sensing or another protocol. The pulse or scan sequence scans the region of the patient, resulting in scan data for a single imaging appointment. In an MR example, a pulse sequence is created based on the configuration of the MR scanner (e.g., the imaging protocol selected). The pulse sequence is transmitted from coils into the patient. The resulting responses are measured by receiving radio frequency signals at the same or different coils. The scanning results in k-space measurements as the scan data.

In act 210, an image processor reconstructs a representation of the patient from the scan data. An object (e.g., anatomy) of the patient is reconstructed. The image processor reconstructs a representation or reconstruction from the scan data of the scan. For MR reconstruction, the k-space data is Fourier transformed into scalar values representing different spatial locations, such as spatial locations representing a plane through or volume of a region in the patient. Scalar pixel or voxel values are reconstructed as the MR image or object. The spatial distribution of measurements in object or image space is formed. This spatial distribution represents the object of the patient.

Various inputs for reconstruction may be used. The scan data is input, such as inputting under-sampled multi-coil k-space data. Coil sensitivity maps and/or an input coil bias field correction map may be input.

The reconstruction is performed using any of various techniques. For example, an optimization is performed to fit the scan data to an estimated representation, such as GRAPPA or other reconstruction algorithm. In other embodiments, the reconstruction uses, at least in part, a machine-learned model, such as a neural network trained with deep machine learning. The machine-learned model is previously trained, and then used as trained in reconstruction. Fixed values of learned parameters are used for application. In application of the already trained network, the reconstruction process is followed.

In one embodiment, the machine-learned model is trained to receive input of the scan data and to output the reconstruction. In other embodiments, the machine-learned model is used in the reconstruction process, such as for applying a Fourier or inverse Fourier transform, determining a gradient, and/or regularization. Optimization is iteratively performed with the machine-learned model contributing to an act or acts (i.e., stages) in each or some of the iterations.

In yet other embodiments, the machine-learned model is part of an unrolled iterative reconstruction. For example, the machine-learned model implements a regularization function in the unrolled iterative reconstruction. An unrolled proximal gradient algorithm with Nesterov momentum includes a convolutional neural network (CNN) for regularization. To produce sharp reconstructions from input under-sampled (compressed sensing) multi-coil (parallel imaging) k-space data, such network is first trained to minimize a combined L1 and a multi-scale version of the structural similarity (SSIM) content losses between network prediction and ground truth images for regularization. Other losses may be used, such as using just the L1 loss. The same or different machine-learned model or network (e.g., CNN) is used for each or some of the unrolled iterations. The CNN for regularization may be refined, such as using a semi-supervised refinement applied in a subsequent training step where an adversarial loss is based on Wasserstein Generative Adversarial Networks (WGAN). In another example, the unrolled iterative reconstruction disclosed in U.S. Patent Publication No. 2022/0180574A1 is used.

The reconstruction may output the representation as pixels, voxels, and/or a display formatted image in response to the input. The learned values and network architecture, with any algorithms (e.g., extrapolation and gradient update) determine the output from the input. The output of the reconstruction, such the output of the machine-learned model, is a two-dimensional distribution of pixels representing an area of the patient and/or a three-dimensional distribution of voxels representing a volume of the patient. The output from the last reconstruction iteration may be used as the output representation of the patient.

Other processing may be performed on the input k-space measurements before input. Other processing may be performed on the output representation or reconstruction, such as spatial filtering, color mapping, and/or display formatting. In one embodiment, the machine-learned network outputs voxels or scalar values for a volume spatial distribution as the medical image. Volume rendering is performed to generate a display image. In alternative embodiments, the machine-learned network outputs the display image directly in response to the input.

Figure 3:
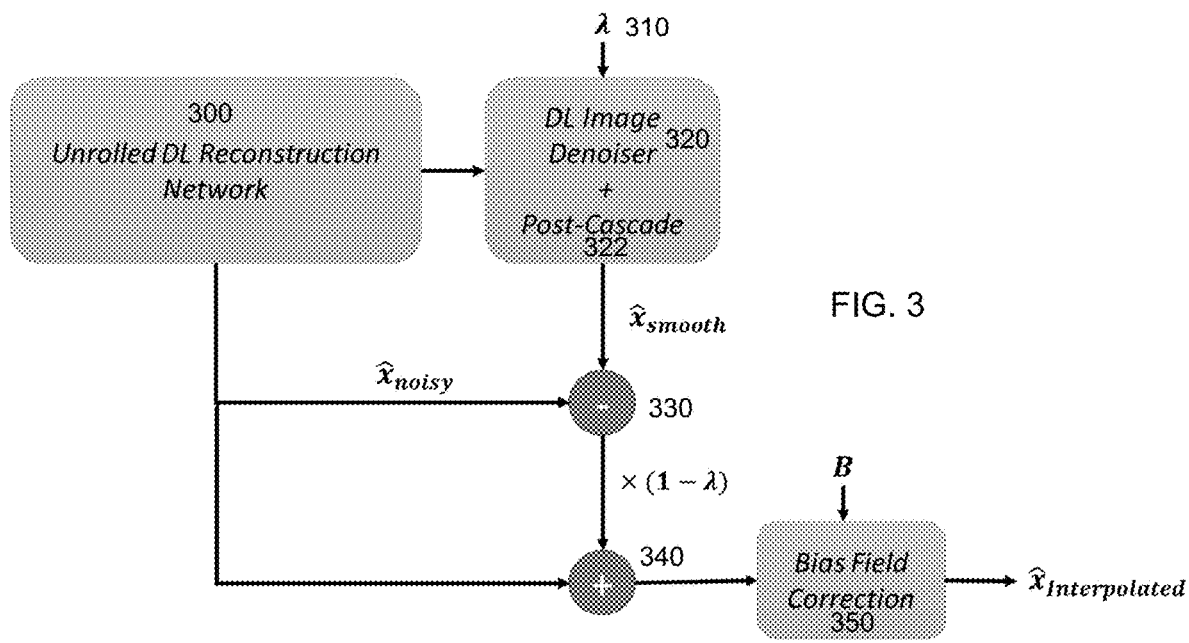
FIG. 3 illustrates the user control of a characteristic of a reconstructed image.

FIG. 3 illustrates an example of the method of FIG. 2, including the reconstruction. In this example, an unrolled deep-learned reconstruction network 300 outputs a reconstruction or representation, $\hat{x}_{noisy}$, to the deep-learned denoiser 320 and for combination through subtraction 330 and/or addition 340.

Returning to FIG. 2, in act 220, the image processor alters a characteristic of the reconstructed object. The reconstruction or representation is provided as one extreme of the characteristic. For example, the representation is considered noisy. Any level of noise, including very little, may be included in the representation. This representation is the extreme end of a range to be provided for selectable levels of noise. The alteration creates the other extreme, such as a representation with less noise.

The alteration is performed, at least in part, by application of the reconstructed object to a machine-learned network. The machine-learned network generates or contributes to generation of the altered representation having a different level of the characteristic. For example, the representation is input to the machine-learned denoising network. The denoising network outputs the altered representation having less noise in response to the input. The reconstruction data (i.e., reconstruction or representation output by act 210) is denoised by application to the machine-learned denoising network. The object is represented by the altered reconstruction data from the denoising.

In the example of FIG. 3, the alteration is performed by the deep-learned denoiser network 320, resulting in the altered representation, $\hat{x}_{smooth}$. The post cascade 322 has a gradient step with a step size fixed to one to perform data-consistency (i.e., replacing the k-space samples for which there are measurements with their corresponding measurements). This altered representation is provided for subtraction 330. $\hat{x}_{noisy}$ is the original noisy output representation of the reconstruction network 300, and $\hat{x}_{smooth}$ is the new smooth output of the denoiser network 320.

Any of various machine-learned models may be used, such as a neural network or support vector machine. In one embodiment, the machine-learned network for denoising is an image-to-image network. Data representing a spatial distribution (e.g., the original reconstruction) is input, and the image-to-image network outputs a spatial distribution (e.g., the altered reconstruction). An example image-to-image network is a U-Net, but other CNN or fully connected networks (FCN) may be used. The machine-learned denoising network may be a deep-learned network.

In one embodiment, the machine-learned network is an image-to-image network formed as a deep iterative hierarchal network (DIHN) for the denoising or alteration of another characteristic or characteristics. For example, the CNN disclosed in U.S. Patent Publication No. 2022/0180574A1 for reconstruction is trained and used instead as the machine-learned denoiser network.

Figure 4:
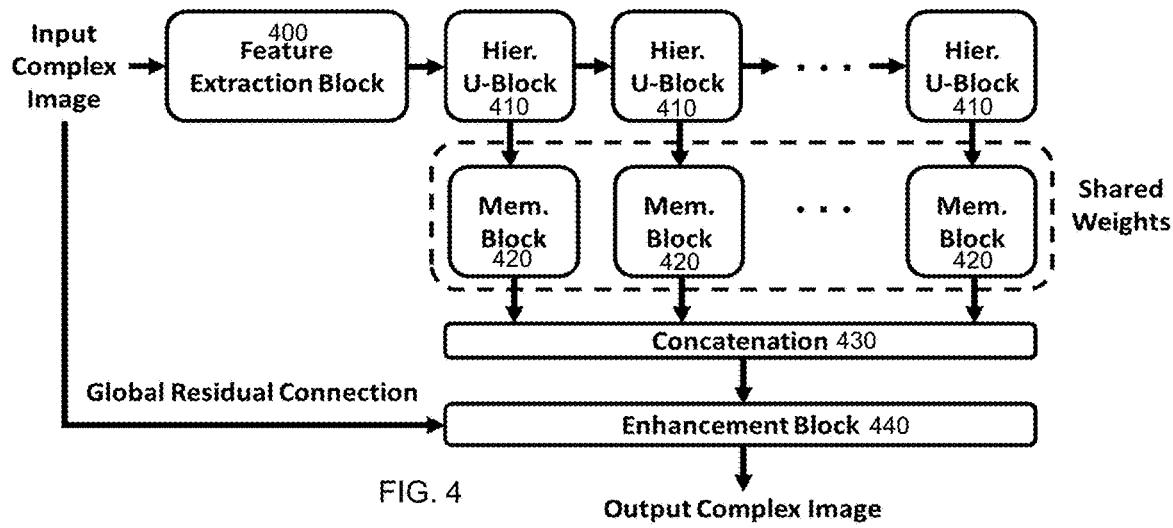
FIG. 4 is a block diagram of one embodiment of a machine-learned network for altering a characteristic.
Figure 5:
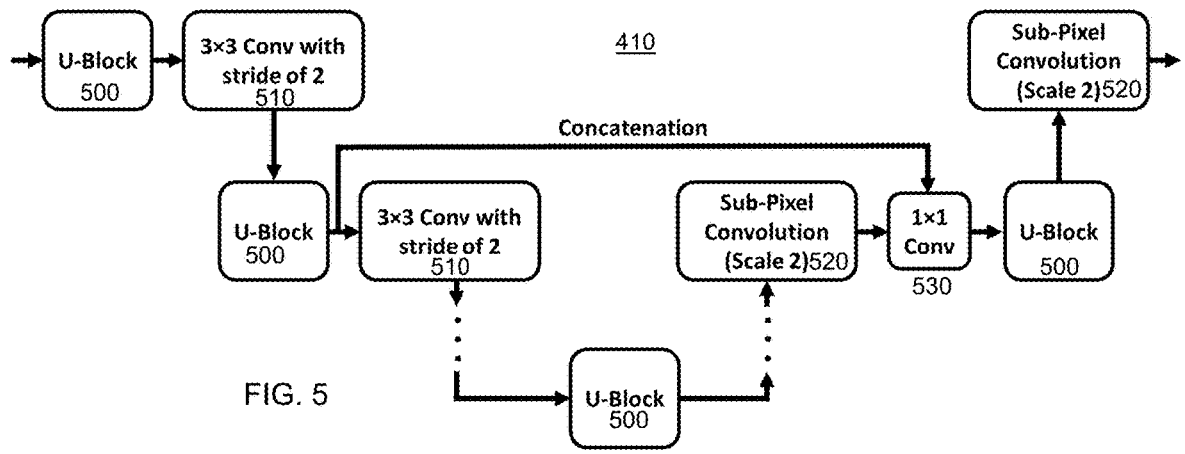
FIG. 5 is a block diagram of one embodiment of a hierarchal U-block network of the machine-learned network of FIG. 4.
Figure 6:
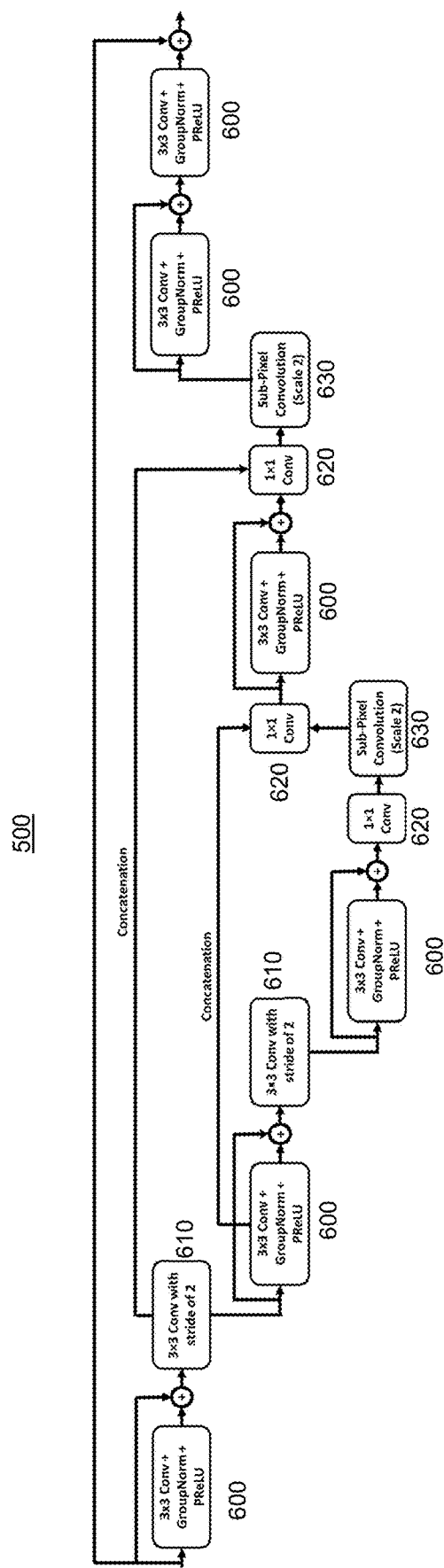
FIG. 6 is a block diagram of one embodiment of a U-block network of the hierarchal U-block network of FIG. 5.

FIGS. 4-6 show an example DIHN used as the machine-learned network for denoising in the alteration of act 220. The deep-learned image denoiser is based on an image-to-image translation network with a hierarchical design that iteratively down-samples the input image feature maps followed by an up-sampling procedure. The DIHN is designed to ensure the system being fast and memory-efficient while also robust to variations in signal intensities and contrasts (e.g., due to different scanned organs, acquisition parameters, image resolutions, etc.).

FIG. 4 shows a series of hierarchal U-blocks 410. Each hierarchal U-block 410 is a convolution neural network. The initial hierarchal U-block 410 receives the complex image, features output by the feature extraction block 400, and/or a combination thereof as input. The initial hierarchal U-block 410 outputs to the next hierarchal U-block 410 in the unrolled series and outputs to a memory block 420. Each successive hierarchal U-block 410 receives input from the previous hierarchal U-block 410 and outputs to the next hierarchal U-block 410 and the memory block 420. The last hierarchal U-block 410 of the series outputs to the memory block 420. Any number of hierarchal U-blocks 410 may be provided, such as two, three, four, eight, twelve, or sixteen.

In training, each hierarchal U-block 410 is a separate network with the same architecture. As a result, the same learnable parameter may have a different learned value for one hierarchal U-block 410 as compared to any others of the hierarchal U-blocks 410. In other embodiments, the architecture also varies so that different architectures are provided for different ones of the hierarchal U-blocks 304.

The hierarchal U-blocks 410 are hierarchal. In one embodiment, each of the iterative U-blocks 410 (e.g., CNNs) are hierarchal. One or more other blocks and/or iterative U-blocks 410, which are not hierarchal, may be provided.

FIGS. 5 and 6 show an example hierarchal U-block 410 implemented as a CNN. The hierarchal U-block 410 includes nested down-sampling and up-sampling. For example, FIG. 5 shows the hierarchal U-block 410 as including U-blocks 500, each of which also includes down-sampling followed by up-sampling. The result is a hierarchy of down and up-sampling at one or more resolution levels within down and up-sampling. The interior down and up-sampling blocks operate on reduced resolution data, so are less computationally and memory expensive.

The hierarchal U-block 410 of at least one iteration of regularization includes U-blocks 500. These U-blocks 500 are provided at different levels of the down and up-sampling of the hierarchal U-block 410. In the example architecture of FIG. 5, a U-block 500 receives the input. A 3×3 or other sized convolution layer 510 with a stride of 2 or other stride downs samples the output of the initial U-block 500. The convolution layer 510 outputs to another U-block 500, which outputs to another 3×3 or other sized convolution layer 510 with a stride of 2 or other stride and outputs to a concatenation. The convolution layer 510 down samples, and outputs to one or more additional layers or levels of U-blocks 500 and convolution layers for down sampling.

The down sampling continues until the lowest level or resolution U-block 500 is reached at the bottleneck of the hierarchal U-block 410. Similarly, corresponding up-sampling provided by sub-pixel convolution layers 520 with intervening U-blocks 500 is provided. A U-block 500 is not provided at the output but may be. While a scale of 2 is shown, other up-sampling scales may be used.

The concatenation may be a convolution layer or other structure. The concatenation generates additional features, providing more output features than input to the concatenation. In alternative embodiments, the number of features is not increased, a skip connection without any network layers, a residual connect layer (e.g., sum), or other operation is provided. While only one concatenation is shown for one level or resolution (scale), other concatenations at other levels may be provided. The concatenation is parallel with the bottleneck, skipping part of the network to pass between the down sampling chain and the up-sampling chain at a same resolution.

In this machine-learned model of FIG. 4, the extracted features are passed through several hierarchal U-blocks 410 of FIG. 4. The hierarchal U-blocks 410 are composed of a several U-blocks 500 interspersed with down-sampling, allowing efficient processing at a coarser scale before up-sampling the processed feature maps using subpixel convolutions. Each U-block 500 itself includes an architecture that has down-sampling, followed by up-sampling.

FIG. 6 shows an example CNN architecture for each U-block 500. All the U-blocks 500 may have the same or different architecture. The down-sampling chain includes layers 600 with convolution (e.g., 3×3), group normalization, and PReLU activation and down sampling convolution layers 610 with any stride (e.g., 2). The up-sampling chain after the bottle neck (i.e., lowest scale) includes layers 600 as well as 1×1 convolutions 620 and sup-pixel convolutions 630 with any scale (e.g., 2).

Group normalization is used, but batch or other normalization layers may be provided instead. PReLU activation is used to provide the network with additional modeling flexibility, but ReLU, leaky ReLU, or other activation functions may be used. Sub-pixel convolutions are used for upscaling the feature maps for computational efficiency, but transposed convolutions with the desired scale may alternatively be used to additionally increase the model flexibility.

The U-block 500 includes concatenation at the different scales. A global connection is included, so that the input is passed to the output. Local connections connect inputs to outputs for the convolution layers 600. These local and global connections are skip connections passing the inputs to be summed with the outputs of the convolution layers 600 and the entire U-block 500, respectively. The local and global residual connections enhance information flow while maintaining efficient memory usage, such as compared to dense connections.

Other architectures for the U-block 500 may be used. Other hierarchal architectures for the hierarchal U-blocks 410 may be used. Other iterative architectures of the machine-learned model 300 for regularization may be used.

Returning to FIG. 4, the machine-learned model includes the memory block 420. The memory block 420 is formed from convolution layers, such as being a CNN. The memory block 420 does not but may include down-sampling and/or up-sampling. In one embodiment, the memory block 420 includes the architecture of the U-block 500 without the convolution layers 610 and without the convolution layers 630. Other architectures may be used.

FIG. 4 shows separate memory blocks 420 with shared weights. The same memory block 420 is applied separately to the outputs of the different hierarchal U-blocks 410. Alternatively, separate memory blocks 420 are trained for the separate or iterative hierarchal U-blocks 410. The memory block 420 is provided to combine the outputs of the hierarchical U-blocks 410. The memory block 420 may extract features from the output of the hierarchal U-blocks 410 and/or from different scales within the hierarchal U-blocks 410. The memory block 420 processes the extracted feature maps at different levels.

The machine-learned model includes a concatenation 430. The concatenation 430 is a memory storing a collection of the features output by the memory block 420. The memory block 420 concatenates the memory block outputs before passing the features to the final enhancement block 440. The concatenation 430 is formed from neural network layers in other embodiments, such as providing further convolution layers.

The machine-learned model includes an enhancement block 440. The enhancement block 440 is one or more convolution layers to refine the output. In one embodiment, 1×1 convolution is used to fuse the concatenated representations. Where the feature extraction block 400 includes down-sampling without a corresponding up-sampling, the enhancement block 440 includes a sub-pixel convolution layer to generate the final complex output image at the resolution or scale of the input to the machine-learned denoising model. A global residual connection may input the input image to the enhancement block 440. The enhancement block 440 receives a concatenation 430 of outputs of the memory block 420 and the input image and outputs the medical image as regularized.

The image denoiser network design based on the DIHN architecture allows for a good trade-off between inference speed and denoising performance. Also, DIHN is more memory-efficient than conventional U-Net architectures as most of the computations are on a coarser scale (20-30% less GPU memory). Moving the computation to a coarser level has not shown any limitation on analysis at the finest scale due to the hierarchical design of DIHN, allowing for efficient and accurate image denoising in heterogeneous MRI datasets.

The output is the altered representation, such as with less noise. The machine-learned network may be trained to alter any of various characteristics, such as anatomy visibility, sharpness, contrast, noise, dynamic range, edge definition, and/or color. The DIHN architecture is trained, in one embodiment, to smooth the noisy prediction from a reconstruction using a deep machine-learned model.

The learnable parameters of the architecture of the model are trained for altering the characteristic or characteristics, such as for denoising (removing or reducing noise). Where the reconstruction also includes a machine-learned model, the machine-learned denoising network is trained independently of the machine-learned model for reconstruction. In training and application, the machine-learned denoising network uses outputs of the machine-learned model for reconstruction with the weights of the machine-learned model for reconstruction fixed (previously trained) in the training of the machine-learned denoising network. The deep-learned image denoiser is trained independently on the deep learned reconstruction network outputs with the deep-learned reconstruction network weights fixed. The deep-learned image denoiser is trained to minimize the L1 loss between denoised prediction and ground truth representations.

In the compressed sensing embodiment, the ground truth representation for training may be reconstructions formed from full sampling, so having reduced noise. Other ground truth representations may be used, such as generated by simulation or application of a denoising or other characteristic altering algorithm.

The machine-learned denoising model is trained for application. The training data includes many sets of data, such as representations output by reconstruction and the corresponding ground truth. Tens, hundreds, or thousands of samples are acquired, such as from scans of volunteers or patients, scans of phantoms, simulation of scanning, and/or by image processing to create further samples. Many examples that may result from different scan settings, patient anatomy, scanner characteristics, or other variance that results in different samples are used. In one embodiment, an already gathered or created MR dataset is used for the training data. The samples are used in machine learning (e.g., deep learning) to determine the values of the learnable variables (e.g., values for convolution kernels) that produce outputs with minimized cost or loss across the variance of the different samples.

A computer (e.g., image processor) machine trains the model for altering the representation. For example, the neural network of FIGS. 4-6 is machine trained for denoising using the training data, including many input samples of sets of relatively noisy reconstructions and corresponding relatively less noisy ground truth outputs. In one embodiment, deep learning is used to train the model. The training learns both the features of the input data and the conversion of those features to the desired output (i.e., denoised data). Backpropagation, RMSprop, ADAM, or another optimization is used in learning the values of the learnable parameters of the network (e.g., the convolutional neural network (CNN) or fully connection network (FCN)). Where the training is supervised, the differences (e.g., L1, L2, mean square error, or other loss) between the estimated output and the ground truth output are minimized.

Any architecture or layer structure for machine learning to perform an operation for separately reconstructing from subsets may be used. For example, any of the architectures discussed for FIGS. 4-6 may be used. The architecture defines the structure, learnable parameters, and relationships between parameters. In one embodiment, a convolutional or another neural network is used. Any number of layers and nodes within layers may be used. A DenseNet, U-Net, encoder-decoder, Deep Iterative Down-Up CNN, image-to-image and/or another network may be used. Some of the network may include dense blocks (i.e., multiple layers in sequence outputting to the next layer as well as the final layer in the dense block). Any know known or later developed neural network may be used. Any number of hidden layers may be provided between the input layer and output layer.

Machine learning is an offline training phase where the goal is to identify an optimal set of values of learnable parameters of the model that can be applied to many different inputs. These machine-learned parameters can subsequently be used during clinical operation to alter the characteristic. Once learned, the machine-learned model is used in an online processing phase in which a reconstruction for a given patient is altered.

Referring again to FIG. 2, in act 230, the image processor receives an input of a level of characteristic. The input is received from an interface and/or a user input device. For example, a user, facility, or default setting for the level is received as an input from memory. An initial value may be loaded or provided as the input. As another example, a user enters the level, such as through selection along a scale, entry of a value, depression of a button, or rotation of a control knob. The value may be altered, such as receiving the user-selected level of denoising as an adjustment to tune the output or displayed image based on a previous value of the user-selected level of denoising.

A level of the characteristics, such as denoising, is received. The input is a value within a range. For example, the input is for a continuous variable in the range of [0,1]. Other ranges may be used. The extremes of the range represent the available extremes of the characteristic, such as 0 being smoothest (less noise) and 1 being noisiest (most noise). Non-continuous variables may be used. FIG. 3 shows receipt of the value, λ, as the input. λ is the input user-defined denoising level in the range of [0,1] in one example. In other embodiments, the user selection and input vary spatially, such as the user selecting a map of different levels of alteration by location or selecting different levels by spatial position.

In act 240 of FIG. 2, the image processor combines the reconstructed object with an output of the machine-learned network. Any combination function may be used, such as addition, subtraction, multiplication, and/or division. In one embodiment, the combination is a linear interpolation between the original representation and the altered representation. Non-linear functions may be used.

The combination is based on the input level of the characteristic. For example, the combination is to provide the input level of denoising. In response to the user inputting a desired relative amount of noise, the combination is performed to provide that amount of noise. The combination may vary by location, such as using different weights at different locations.

In one embodiment, the input level is used as a weight for the combination, such as a weighted average of the two representations. In other embodiments, the input level is mapped to the combination function or values used in the combination. In yet other embodiments, the input level is used to adjust or set an amount of contribution of the alteration.

FIG. 3 shows an example combination of the original reconstruction, $\hat{x}_{noise}$, with the altered reconstruction, $\hat{x}_{smooth}$. A difference 330 between the original reconstruction, $\hat{x}_{noise}$, with the altered reconstruction, $\hat{x}_{smooth}$ is found. This difference represents the change from noisy to smooth (i.e., the alteration provided by the denoising network). The input value of the continuous variable is subtracted from one, with the result being multiplied with the difference 330. This weighted result is added 340 to the original reconstruction. At inference time, the final output is a linear interpolation between the noisy output and its corresponding denoised output (the output here is an image, but it can also be (multicoil) k-space), allowing the user to tune the desired preference's output noise level.

In some embodiments, a bias field correction 350 based on the bias field, B, in MR is applied to the result of the combination. After any other processing, the final representation, $\hat{x}_{interpolated}$, is output. The final representation is the interpolated output based on the input noise level λ.

In act 250 of FIG. 2, the image processor generates and displays an image of the object from the output combined representation. The combined reconstruction with the desired level of the characteristic is used to generate an image. The image has a level of the characteristic (e.g., level of noise relative to sharpness) based on the user-selected level (e.g., of denoising).

The resulting combination representation or image is then rendered to a two-dimensional display. A display (e.g., display screen or device) displays the medical image, such as the MR image formed by the combination. The medical image, after or as part of any post processing, is formatted for display on the display. The display presents the image for viewing by the user, radiologist, physician, clinician, and/or patient. The image assists in diagnosis, prognosis, and/or therapy.

The displayed image may represent a planar region or area in the patient. Alternatively, or additionally, the displayed image is a volume or surface rendering from voxels (three-dimensional distribution) to the two-dimensional display.

Although the subject matter has been described in terms of exemplary embodiments, it is not limited thereto. Rather, the appended claims should be construed broadly, to include other variants and embodiments, which can be made by those skilled in the art.

What is claimed is:

1. A method of reconstruction for a medical imaging system, the method comprising:
    scanning a patient by the medical imaging system, the scanning acquiring scan data;
    reconstructing an object of the patient from the scan data, the object represented by first reconstruction data from the reconstructing;
    denoising the reconstruction data, the reconstruction data denoised by application to a machine-learned denoising network, the object represented by second reconstruction data from the denoising;
    receiving a user-selected level of denoising;
    combining the first and second reconstruction data based on the user-selected level of denoising; and
    displaying an image of the object from the combination of the first and second reconstruction data.

2. The method of claim 1 wherein scanning comprises magnetic resonance scanning pursuant to a protocol for parallel imaging with compressed sensing.

3. The method of claim 1 wherein reconstructing comprises reconstructing with a machine-learned model.

4. The method of claim 3 wherein reconstructing comprises reconstructing with an unrolled iterative reconstruction where the machine-learned model implements a regularization function of the unrolled iterative reconstruction.

5. The method of claim 3 wherein the machine-learned denoising network was trained independently of the machine-learned model where the machine-learned denoising network used outputs of the machine-learned model with the weights of the machine-learned model fixed in the training of the machine-learned denoising network.

6. The method of claim 1 wherein denoising comprises inputting the first reconstruction data into the machine-learned denoising network, the machine-learned denoising network outputting the second reconstruction data in response to the inputting.

7. The method of claim 1 wherein denoising comprises denoising with the machine-learned denoising network comprising an image-to-image network.

8. The method of claim 7 wherein denoising comprises denoising with the image-to-image network comprising a deep iterative hierarchal network.

9. The method of claim 1 wherein receiving comprises receiving the user-selected level of denoising as a value of a continuous variable in a range of 0,1.

10. The method of claim 1 wherein receiving comprises receiving the user-selected level of denoising as an adjustment to tune the image based on a previous value of the user-selected level of denoising.

11. The method of claim 1 wherein combining comprises linearly interpolating between the first and second reconstruction data.

12. The method of claim 1 wherein displaying comprises displaying the image with a level of noise relative to sharpness based on the user-selected level of denoising.

* * * * *